(12) United States Patent
Kim

(10) Patent No.: US 11,490,046 B2
(45) Date of Patent: Nov. 1, 2022

(54) AROMA SHARING SYSTEM AND AROMA-ADDED CONTENT SHARING SYSTEM

(71) Applicant: AROMAJOIN CORPORATION, Kyoto (JP)

(72) Inventor: Dong Wook Kim, Kyoto (JP)

(73) Assignee: AROMAJOIN CORPORATION, Kyoto (JP)

( * ) Notice: Subject to any disclaimer, the term of this patent is extended or adjusted under 35 U.S.C. 154(b) by 603 days.

(21) Appl. No.: 16/561,245

(22) Filed: Sep. 5, 2019

(65) Prior Publication Data
US 2020/0084411 A1    Mar. 12, 2020

(30) Foreign Application Priority Data

Sep. 6, 2018   (JP) .............................. JP2018-167094
Apr. 24, 2019  (JP) .............................. JP2019-083237

(51) Int. Cl.
*B01D 47/00*    (2006.01)
*H04N 5/93*     (2006.01)
(Continued)

(52) U.S. Cl.
CPC ............ *H04N 5/9305* (2013.01); *A61L 9/125* (2013.01); *H04N 5/04* (2013.01); *A61L 2209/11* (2013.01); *A61L 2209/133* (2013.01)

(58) Field of Classification Search
CPC ........ H04N 5/9305; H04N 5/04; A61L 9/125; A61L 2209/11; A61L 2209/133
(Continued)

(56) References Cited

U.S. PATENT DOCUMENTS 6,282,458 B1 * 8/2001 Murayama .............. A61L 9/122
                                                 700/265
9,821,082 B1 * 11/2017 Swartz .................... A61L 9/035
(Continued)

FOREIGN PATENT DOCUMENTS

JP      07-302080 A    11/1995
JP    2006-201995 A     8/2006
(Continued)

OTHER PUBLICATIONS

Official Communication issued in Japanese Patent Application No. 2018-167094, dated Feb. 26, 2019.
(Continued)

*Primary Examiner* — Zhen Y Wu
(74) *Attorney, Agent, or Firm* — Keating and Bennett, LLP

(57) ABSTRACT

This system includes an olfactory display in which a plurality of aroma source cartridges can be loaded, a terminal device that controls the olfactory display, and a server connected to the terminal device via a network. The terminal device includes a content reproducer that reproduces an aroma-added content downloaded from the server. Aroma reproduction information includes aroma numbers standardized to specify types of aromas. The content reproducer determines which one of the plurality of aroma source cartridges loaded in the olfactory display is to be used to reproduce an aroma based on the aroma number, and allows the aroma to be emitted from the olfactory display based on the aroma reproduction information in synchronization with video and/or sound.

16 Claims, 11 Drawing Sheets

(51) Int. Cl.
*H04N 5/04* (2006.01)
*A61L 9/12* (2006.01)

(58) Field of Classification Search
USPC .......................................................... 261/26
See application file for complete search history.

(56) References Cited

U.S. PATENT DOCUMENTS

| | | | |
|---|---|---|---|
| 2002/0113909 A1* | 8/2002 | Sherwood | H04N 21/4131 348/739 |
| 2012/0066387 A1 | 3/2012 | Park et al. | |
| 2013/0151955 A1* | 6/2013 | Williams | G06F 40/166 715/255 |
| 2014/0189026 A1 | 7/2014 | Tange | |
| 2015/0283282 A1* | 10/2015 | Kim | A61L 9/00 261/96 |
| 2016/0021325 A1* | 1/2016 | Porcar | A61L 9/12 348/553 |
| 2017/0076403 A1* | 3/2017 | Edwards | A61L 9/04 |
| 2017/0253338 A1* | 9/2017 | Fantuzzi | A61L 9/122 |
| 2017/0340764 A1* | 11/2017 | Wong | A61L 9/03 |
| 2018/0036448 A1* | 2/2018 | Becker | A61L 9/12 |
| 2018/0369442 A1* | 12/2018 | Keisen | G06K 7/10297 |
| 2019/0019033 A1* | 1/2019 | Chang | G06V 20/20 |
| 2019/0339654 A1* | 11/2019 | Edwards | A61L 9/02 |
| 2021/0100923 A1* | 4/2021 | Gimeno Asin | B01F 33/8442 |

FOREIGN PATENT DOCUMENTS

| | | |
|---|---|---|
| JP | 2009-193344 A | 8/2009 |
| JP | 2012-198694 A | 10/2012 |
| JP | 2015-125580 A | 7/2015 |
| JP | 2016-522690 A | 8/2016 |
| JP | 6297834 B2 | 3/2018 |
| KR | 10-2012-0026290 A | 3/2012 |
| KR | 10-1173541 B1 | 8/2012 |

OTHER PUBLICATIONS

Official Communication issued in Japanese Patent Application No. 2018-167094, dated Jun. 18, 2019.
Official Communication issued in Japanese Patent Application No. 2019-083237, dated Jul. 23, 2019.
Official Communication issued in corresponding European Patent Application No. 19195474.2, dated Jan. 29, 2020.
Official Communication issued in corresponding European Patent Application No. 19195474.2, dated Apr. 22, 2020.
Aromajoin, "AromaPlayer—Watch your movie with scents included", XP054980369, Retrieved from the Internet: URL: https://www.youtube.com/watch?v=Mo0MSSRWM90, Jan. 23, 2017, pp. 1.

* cited by examiner

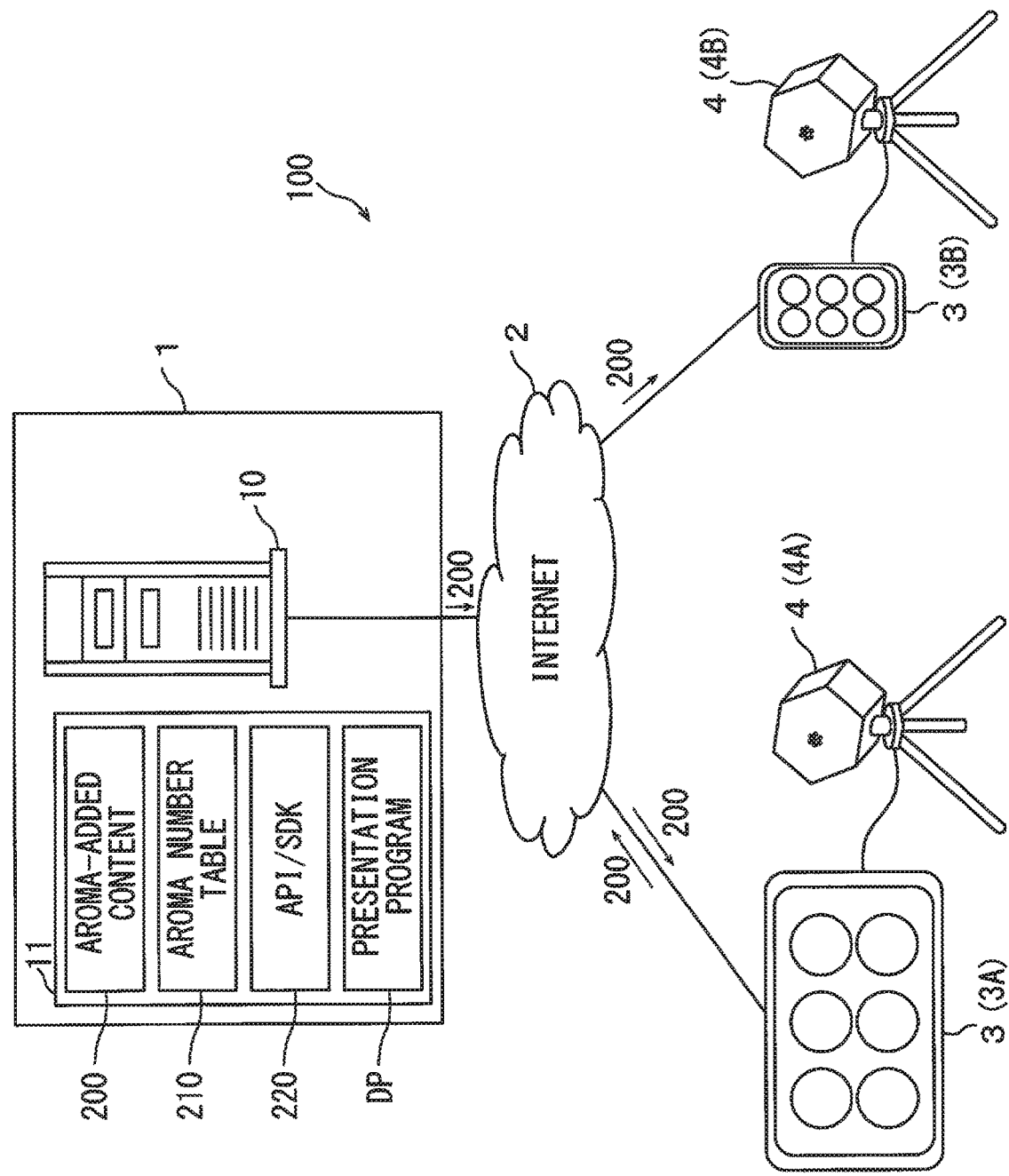
F I G. 1

FIG. 6

| LARGE CLASSIFICATION | | MIDDLE CLASSIFICATION | | SMALL CLASSIFICATION | |
|---|---|---|---|---|---|
| CATEGORY | ABBREVIATION | CATEGORY | ABBREVIATION | CATEGORY | AROMA NUMBER |
| NATURAL | N | CITRUS | CT | BERGAMOT | N-CT1 |
| | | | | CITRONELLA | N-CT2 |
| | | | | GRAPEFRUIT | N-CT3 |
| | | | | KABOSU | N-CT4 |
| | | | | LEMON | N-CT5 |
| | | | | LIME | N-CT6 |
| | | | | ⋮ | ⋮ |
| | | DRINK | DR | | |
| | | FLOWER | FL | | |
| | | FOOD | FD | ⋮ | ⋮ |
| | | FRUIT | FR | | |
| | | GREEN | GN | | |
| | | ⋮ | ⋮ | | |
| SYNTHETIC | S | CITRUS | CT | BERGAMOT | S-CT1 |
| | | | | CITRONELLA | S-CT2 |
| | | | | GRAPEFRUIT | S-CT3 |
| | | | | KABOSU | S-CT4 |
| | | | | LEMON | S-CT5 |
| | | | | LIME | S-CT6 |
| | | | | ⋮ | ⋮ |
| | | DRINK | DR | | |
| | | FLOWER | FL | | |
| | | FOOD | FD | ⋮ | ⋮ |
| | | FRUIT | FR | | |
| | | GREEN | GN | | |
| | | ⋮ | ⋮ | | |

F I G. 1 2

AROMA CODE

ACIN  N-XXX1

DIFFUSE  05:00

DURATION  3S

DENSITY : 70%

AROMA SHARING SYSTEM AND AROMA-ADDED CONTENT SHARING SYSTEM

BACKGROUND OF THE INVENTION

Field of the Invention

The present invention relates to a system for sharing an aroma and, more particularly, to a system for sharing an aroma among different users. Further, the present invention relates to a system for sharing a content to which aroma reproduction information is added.

Description of Related Art

A sense of vision or a sense of hearing, which is a physical sense, is subjected to physical stimulation from light or sound. Thus, contents that stimulate the sense of vision or the sense of hearing can be reproduced based on continuous physical amounts such as a wavelength and a frequency of light, and a frequency and an amplitude of sound. On the other hand, olfaction, which is a chemical sense, identifies patterns owned by an aroma molecule (such as a shape, size, and a property of a functional group) as discrete information. The aroma molecule is a volatile low molecular organic compound which is sucked into nostrils by a flow of air, dissolved in an olfactory mucosa, and stimulates an olfactory cilia.

As such, it is necessary to prepare in advance a mixture of low molecular organic compounds to be stimulating elements in order to reproduce an aroma that stimulates the olfaction. In order to constitute a device that stimulates olfaction, it is necessary, for example, to load an aroma material to be the stimulating element for olfaction as a cartridge in the interior of the device. As far as such a device has the configuration in which the cartridge is filled with the aroma material, the number of reproduction of the aroma is limited.

In the case of olfaction, there exist 396 types of olfactory receptor genes that correspond to three primary colors of vision (red, green, and blue). Under current circumstances, it is unclear how these olfactory receptor genes react to the aroma molecule. Therefore, under the current circumstances, an aroma mixture (a mixed aroma material) generated in a specific pattern can be reproduced only by mixing aroma materials in the same pattern.

In this way, various restrictions are imposed on the reproduction of aromas that stimulate the olfaction, and olfactory displays have been researched, developed, and operationalized as devices for reproducing aromas under these restrictions. Also in a control application for controlling the olfactory displays, the olfactory displays have been developed under these restrictions. JP 6297834 B2 as described below discloses a system that recommends an aroma-added content to an information processing apparatus connected via a network.

BRIEF SUMMARY OF THE INVENTION

As shown in JP 6297834 B2, a control application for controlling an olfactory display is capable of reproducing aroma information generated in a predetermined pattern in conjunction with video information and sound information (a mixed aroma material with a predetermined mixing rate). When aroma reproduction information generated in some user's environment is shared with another user, there is a problem that aroma is not accurately reproduced in the other user's environment in the cases shown below.

(a) The types of olfactory displays used by the both users are different, and the total number of loaded aroma source accommodating cartridges are different.

(b) The types of olfactory displays used by the both users are the same, but the cartridges are loaded at different addresses (in different cartridge accommodation chambers);

For example, a cartridge of lemon aroma is loaded in a first cartridge accommodation chamber in an olfactory display A, whereas a cartridge of lemon aroma is loaded in a second cartridge accommodation chamber in an olfactory display B.

(c) The types of olfactory displays used by the both users are the same, but no cartridge is loaded at a certain address (in a certain cartridge accommodation chamber) in one of the devices;

For example, the lemon aroma cartridge is loaded in the first cartridge accommodation chamber in the olfactory display A, whereas no cartridge is loaded in a first cartridge accommodation chamber in the olfactory display B.

(d) The types of olfactory displays used by the both users are the same, but a different cartridge is loaded at a certain address (in a certain cartridge accommodation chamber);

For example, the cartridge of lemon aroma is loaded in the first cartridge accommodation chamber in the olfactory display A, whereas a cartridge of jasmine aroma is loaded in the first cartridge accommodation chamber in the olfactory display B.

(e) The aforementioned conditions (a) to (d) are included, and aromas are reproduced by coupling a plurality of olfactory displays.

An object of an aroma sharing system according to the present invention is to provide a mechanism capable of sharing an aroma among different users even under the environments subjected to the restrictions as described above. Furthermore, an object of an aroma-added content sharing system according to the present invention is to provide a mechanism for sharing a content in which an aroma is added to video information and/or sound information among different users even under the environments subjected to the restrictions as described above.

(1) An aroma sharing system according to the present invention includes a plurality of olfactory units, and a network that connects the plurality of olfactory units. Each olfactory unit includes an olfactory display in which a plurality of aroma source cartridges can be loaded, and a terminal device that controls the olfactory display. The terminal device includes a reproducer that reproduces an aroma based on aroma reproduction information including an aroma number standardized in the system in order to specify a type of the aroma to be reproduced. The reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information. Each olfactory unit transmits the aroma reproduction information to a different olfactory unit via the network to share the aroma reproduction information with the different olfactory unit.

The terminal device reproduces the aroma based on the aroma reproduction information including the standardized aroma number. Therefore, the aroma specified by the aroma reproduction information can be reproduced even in different environments such as the case where the addresses of the aroma source cartridges loaded in the olfactory displays are different, the case where the number of the aroma source cartridges loadable in the olfactory displays is different, and the like.

Thus, reproducibility of the aroma can be enhanced even in various environments such as the case where the types of the olfactory displays are different, the case where the loading states of the aroma source cartridges are different, and the like. The aroma intended by a person who has edited and generated the aroma reproduction information can be emitted.

(2) An aroma sharing system according to the present invention includes a plurality of olfactory units, a network that connects the plurality of olfactory units, and a server connected to the network. Each olfactory unit includes an olfactory display in which a plurality of aroma source cartridges can be loaded, and a terminal device that controls the olfactory display. The server includes a storage that stores aroma reproduction information including an aroma number standardized in the system in order to specify a type of an aroma to be reproduced. The terminal device includes a reproducer that reproduces an aroma based on the aroma reproduction information downloaded from the server. The reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information. Each olfactory unit transmits the aroma reproduction information to a different olfactory unit via the server to share the aroma reproduction information with the different olfactory unit.

The terminal devices can share the aroma reproduction information including the aroma number standardized via the server. Thus, the aroma specified by the aroma reproduction information can be reproduced even in different environments such as the case where the addresses of the aroma source cartridges loaded in the olfactory displays are different, the case where the number of the aroma source cartridges loadable in the olfactory displays is different, and the like.

(3) At least one of the terminal devices includes a generator that edits the aroma reproduction information including the aroma number standardized in the system and generates the edited aroma reproduction information.

The terminal device can generate the aroma reproduction information shared in the system. A user who utilizes the terminal device can generate his/her favorite aroma or an aroma meeting his/her request.

(4) The olfactory display includes a plurality of cartridge accommodation chambers for loading the plurality of aroma source cartridges in the chambers. The terminal device includes a setter that sets a type of an aroma filled in each aroma source cartridge loaded in each cartridge accommodation chamber by using the aroma number.

Even if the aroma source cartridge is loaded in any cartridge accommodation chamber, the terminal device can grasp the location where the aroma source cartridge is loaded. Thus, it is possible to select the aroma source cartridge specified by the aroma reproduction information to reproduce an appropriate aroma.

(5) When the aroma source cartridge for reproducing an aroma corresponding to the aroma number recorded in the aroma reproduction information is not loaded in the olfactory display, the reproducer determines to use an aroma source cartridge for reproducing an aroma approximate (or close) to the corresponding aroma to reproduce the approximate (or close) aroma by utilizing a preset algorithm.

Even if the aroma source cartridge, filled with the aroma identical to the aroma number included in the aroma reproduction information, is not loaded in the olfactory display, it is possible to determine to use the aroma source cartridge for reproducing the approximate (or close) aroma to reproduce the aroma approximate (or close) to the aroma intended by the person who has edited and generated the aroma reproduction information by utilizing the preset algorithm.

(6) The aroma sharing system transmits the aroma reproduction information generated by the generator of the terminal device to another terminal device.

The user who utilizes the terminal device can transmit his/her favorite aroma or an aroma generated at his/her request. Thus, the aroma generated by the user can be shared in the system.

(7) An aroma-added content sharing system according to the present invention is a system that shares an aroma-added content for reproducing an aroma synchronized with video information and/or sound information, and includes a plurality of olfactory units, and a network that connects the plurality of olfactory units. Each olfactory unit includes an olfactory display in which a plurality of aroma source cartridges can be loaded, and a terminal device that controls the olfactory display. The terminal device includes a content reproducer that reproduces an aroma-added content including aroma reproduction information synchronized with video information and/or sound information. The aroma reproduction information includes an aroma number standardized in the system in order to specify a type of an aroma to be reproduced. The content reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information in synchronization with the video information and/or the sound information. Each olfactory unit transmits the aroma-added content including the aroma reproduction information to a different olfactory unit via the network to share the aroma-added content with the different olfactory unit.

The terminal device reproduces the aroma-added content based on the aroma reproduction information including the standardized aroma number. Thus, it is possible to reproduce the aroma-added content even in different environments such as the case where the addresses of the aroma source cartridges loaded in the olfactory displays are different, the case where the number of the aroma source cartridges loadable in the olfactory displays is different, and the like.

Thus, the reproducibility of the aroma-added content can be enhanced even in various environments such as the case where the types of the olfactory displays are different, the case where the loading states of the aroma source cartridges are different, and the like. The aroma intended by a person who has edited and generated the aroma-added content can be emitted, and the utilization of the aroma-added content is promoted.

(8) An aroma-added content sharing system according to the present invention is a system that shares an aroma-added content for reproducing an aroma synchronized with video information and/or sound information, and includes a plurality of olfactory units, a network that connects the plurality of olfactory units, and a server connected to the network. Each olfactory unit includes an olfactory display in which a plurality of aroma source cartridges can be loaded, and a terminal device that controls the olfactory display. The server includes a storage that stores an aroma-added content including aroma reproduction information synchronized with video information and/or sound information. The terminal device includes a content reproducer that reproduces the aroma-added content downloaded from the server. The aroma reproduction information includes an aroma number standardized in the system in order to specify a type of an aroma to be reproduced. The content reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information in synchronization with the video information and/or the sound information. Each olfactory unit transmits the aroma-added content including the aroma reproduction information to a different olfactory unit via the server to share the aroma-added content with the different olfactory unit.

The terminal devices can share the aroma-added content based on the aroma reproduction information including the aroma number standardized via the server. Thus, the aroma-added content can be reproduced even in different environments such as the case where the addresses of the aroma source cartridges loaded in the olfactory displays are different, the case where the number of the aroma source cartridges loadable in the olfactory displays is different, and the like.

(9) At least one of the terminal devices includes a content generator that edits the aroma reproduction information including the aroma number standardized in the system, and edits the aroma-added content including the aroma reproduction information synchronized with the video information and/or the sound information to generate the edited aroma-added content.

The terminal device can generate the aroma-added content including the aroma reproduction information shared in the system. The user who utilizes the terminal device can edit the content, in which his/her favorite aroma or the aroma meeting his/her request is synchronized with the video information and/or the sound information, and can generate the edited content.

(10) The aroma-added content sharing system transmits the aroma-added content including the aroma reproduction information generated by the content generator of the terminal device to another terminal device.

The user who utilizes the terminal device can transmit the aroma-added content including the aroma reproduction information to the other terminal device. Thus, the content, in which the aroma generated by the user is synchronized with the video information and/or the sound information, can be shared in the system.

(11) The aroma-added content sharing system includes a platform that provides for an Application Programming Interface (API) for incorporating the aroma-added content stored in the server so that the incorporated aroma-added content can be reproduced in another information publishing system.

The user can bury the aroma-added content in various applications so that the buried aroma-added content can be reproduced by utilizing the Application Programming Interface stored in the server. The user can publish the aroma-added content in a social networking service (SNS) or a blog, for example.

(12) The server includes a presenter that acquires the aroma number of the aroma filled in the aroma source cartridge loaded in the olfactory display to present to the terminal device a list of the aroma-added contents recommended to be reproduced in the terminal device.

The various aroma source cartridges are loaded by the user in the olfactory display connected to the terminal device. The presenter presents the recommended contents, thereby making it possible to provide highly reproducible aroma-added contents depending on the user's environments.

Other features, elements, characteristics, and advantages of the present invention will become more apparent from the following description of preferred embodiments of the present invention with reference to the attached drawings.

BRIEF DESCRIPTION OF THE SEVERAL VIEWS OF THE DRAWING

FIG. 1 is an overall view of a content sharing system according to the present embodiment;

FIG. 6 is a diagram showing a standardized aroma number table;

FIG. 12 is a diagram showing an aroma code;

DESCRIPTION OF THE PREFERRED EMBODIMENTS

Figure 2:
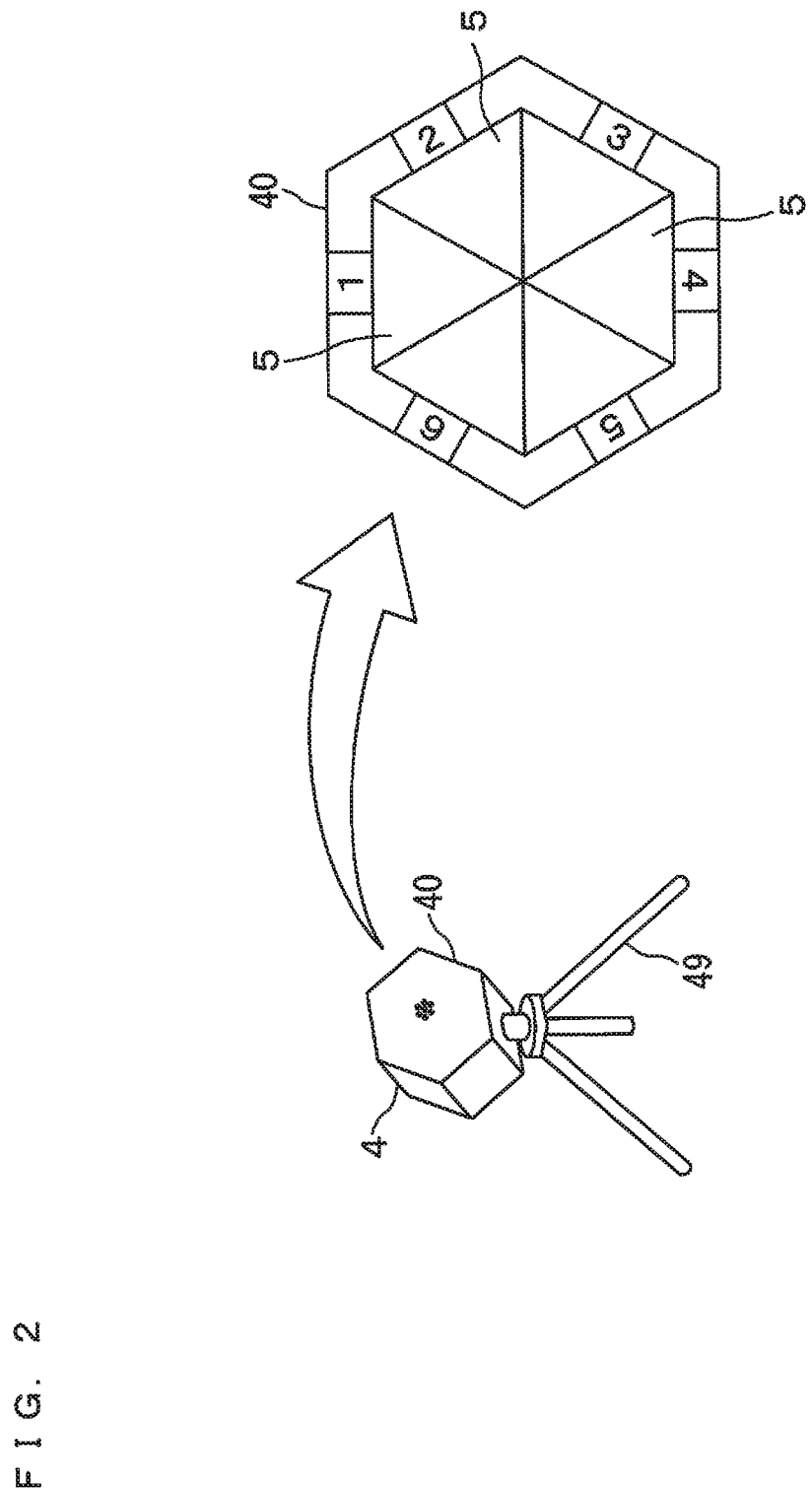
FIG. 2 is an overview of an olfactory display and a schematic view of a display main body.

A configuration of a content sharing system 100 according to an embodiment of the present invention will be described below with reference to the drawing. The content sharing system 100 according to the present embodiment is a system that shares via a network an aroma-added content 200 in which aroma reproduction information is added in addition to video information and sound information. While an embodiment in which an aroma is shared among different users using the aroma-added content 200 will be explained herein, the present invention is also applicable to a system for sharing only an aroma that is not added to video information and sound information.

{1. Summary of Entire System of Content Sharing System}

FIG. 1 is an overall view of the content sharing system 100 according to the embodiment of the present invention. The content sharing system 100 includes a content providing site 1, Internet 2, a terminal device 3, an olfactory display 4, and the like. A server 10 provided in the content providing site 1 is connected to the Internet 2. The server 10 is a server that distributes an aroma-added content 200 in which aroma reproduction information is added in addition to video information and sound information.

The terminal device 3 is a terminal that reproduces the aroma-added content 200 distributed by the server 10. In FIG. 1, two terminal devices 3A, 3B are connected as the terminal device 3. The olfactory display 4 is a device that emits an aroma when the aroma-added content 200 is reproduced in the terminal device 3. In FIG. 1, an olfactory display 4A is connected to the terminal device 3A, and an olfactory display 4B is connected to the terminal device 3B. In the following explanation, when no particular distinction is made between the terminal devices 3A and 3B, the terminal devices 3A, 3B are collectively referred to as the terminal device 3. When no particular distinction is made between the olfactory displays 4A, 4B, the olfactory displays 4A, 4B are collectively referred to as the olfactory display 4. The terminal device 3 and the olfactory display 4 constitute an "olfactory unit" of the present invention.

In the present embodiment, the terminal device 3A is a tablet, and the terminal device 3B is a smartphone. The terminal device 3 is not limited to the tablet or the smartphone, and various terminals that can be connected via a network such as personal computers can be utilized as the terminal device 3.

While it is configured that one olfactory display 4 is connected to one terminal device 3 in the present embodiment, a plurality of olfactory displays 4 may be connected to one terminal device 3. Alternatively, it may also be configured that a plurality of terminal devices 3 are connected to one olfactory display 4, and these terminal devices 3 share the one olfactory display 4. As the terminal device 3, there are two types of devices: one having only a function of reproducing the aroma-added content 200; and the other having a function of editing and generating the aroma-added content 200 in addition to the reproduction function of the aroma-added content 200. In the present embodiment, both of the terminal devices 3A and 3B have the edition generation function in addition to the reproduction function of the aroma-added content 200.

{2. Configuration of Olfactory Display}

FIG. 2 is a diagram showing the olfactory display 4. The olfactory display 4 includes a display main body 40 that emits an aroma, and a tripod 49 that supports the display main body 40. The olfactory display 4 is connected to the terminal device 3 via a USB (Universal Serial Bus) cable in the present embodiment. A connection form between the olfactory display 4 and the terminal device 3 is not particularly limited. The olfactory display 4 may be connected to the terminal device 3 by utilizing wireless communication such as Bluetooth (trademark).

As shown in FIG. 2, six aroma source cartridges 5, 5 . . . can be loaded in the display main body 40 of the olfactory display 4. Components of aromas to be emitted by the olfactory display 4 are filled in the aroma source cartridges 5. While the six aroma source cartridges 5 can be loaded in the olfactory display 4 in the present embodiment, the number of aroma source cartridges 5, which can be loaded, is not limited to this. As shown in FIG. 2, cartridge accommodation chamber numbers are printed on the display main body 40. Since the six aroma source cartridges 5 can be loaded in the olfactory display 4 of the present embodiment, cartridge accommodation chamber numbers {1} to {6} are respectively printed on the corresponding cartridge accommodation chambers, in which the corresponding six aroma source cartridges 5 are loaded.

Figure 3:
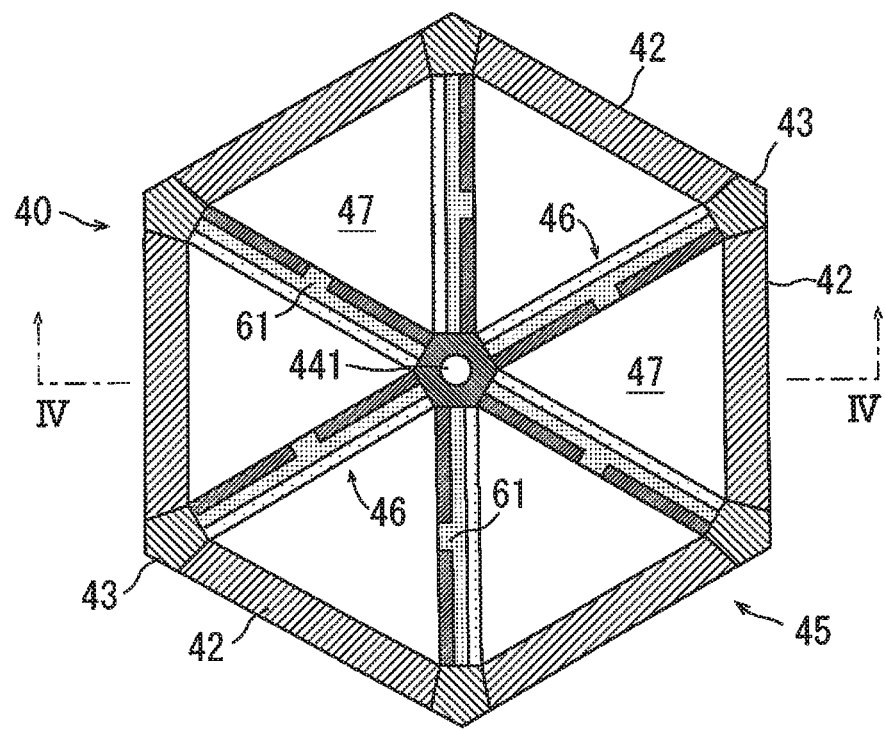
FIG. 3 is a front view of the display main body.

FIG. 3 is a front view showing an internal structure of the display main body 40 of the olfactory display 4. FIG. 3 shows a state where an emission plate 44 (shown in FIG. 4) included in the display main body 40 is removed. Further, FIG. 3 shows a state where no aroma source cartridge 5 is loaded in the display main body 40.

The display main body 40 includes a casing 45, and partitions 46, 46 . . . that divide an internal space of the casing 45 into six chambers. The six sections divided by the partitions 46, 46 . . . form six cartridge accommodation chambers 47, 47 . . . .

Figure 4:
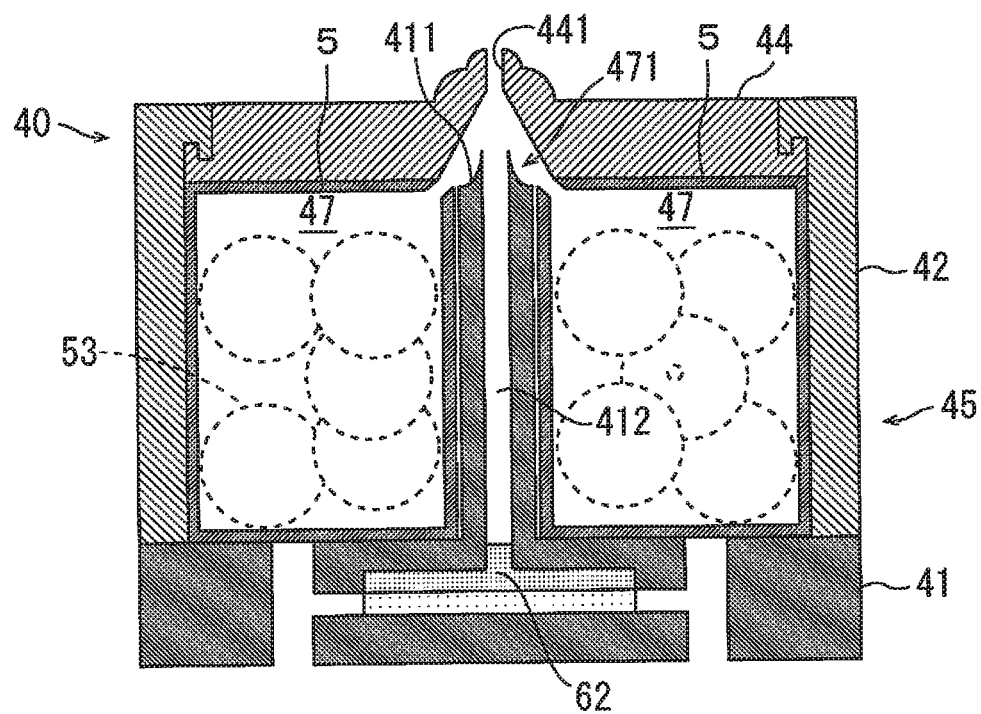
FIG. 4 is a side cross-sectional view of the display main body taken along the VI-VI line.

FIG. 4 is a side cross-sectional view of the display main body 40 taken along the line IV-IV of FIG. 3. The casing 45 includes a base 41, sliding covers 42, and the emission plate 44. The base 41, the sliding covers 42, and the emission plate 44 are composed of acrylic resin, for example.

The base 41 is formed in a substantially hexagonal shape when seen in front view, and arranged on a rear side of the casing 45 (opposite side to the user). As shown in FIG. 3, six support struts 43 are provided in a peripheral portion of the base 41, and the sliding covers 42 are each arranged between the support struts 43. The sliding covers 42 are slidable along the support struts 43. With the sliding covers 42 removed, the aroma source cartridges 5 can be loaded in the casing 45.

The emission plate 44 is attached to front ends of the support struts 43 and the sliding covers 42, i.e., a front end of the casing 45. The emission plate 44 is formed in a substantially hexagonal shape. An emission port 441 is formed in a central portion of the emission plate 44.

As shown in FIG. 4, a central member 411 extending forward is planted at a center of the base 41. The central member 411 extends forward from the base 41, and a tip of the central member 411 is located at a position downward of the emission port 441.

An aroma path 471 that is connected to the emission port 441 formed in the emission plate 44 is formed in the cartridge accommodation chamber 47. Thus, aromas emitted from the aroma source cartridges 5 loaded in the cartridge accommodation chambers 47 are delivered to the emission port 441 through the aroma path 471.

As shown in FIG. 3, airflow sources 61 for allowing the aromas to be emitted from the cartridges 5 are arranged in the partitions 46. That is, six airflow sources 61, 61 . . . are accommodated respectively in the six partitions 46, 46 . . . in the present embodiment. A discharge port of a nozzle provided at a center of each airflow source 61 is connected to the interior of each cartridge accommodation chamber 47 to allow air to flow into the corresponding aroma source cartridge 5 loaded in the corresponding cartridge accommodation chamber 47. In the present embodiment, each airflow source 61 is constituted by a diaphragm utilizing a piezoelectric element (piezo element). By applying a high-frequency alternating voltage or pulse voltage to the piezoelectric element, the diaphragm is bent and vibrated at a high speed in a thickness direction thereof to generate an airflow.

As shown in FIG. 4, an auxiliary airflow source 62 is provided in the base 41. The auxiliary airflow source 62 is provided independently of the cartridge accommodation chambers 47 and is utilized for acceleration of aromas, density adjustment of aroma components, aroma elimination, and the like. In the present embodiment, the auxiliary airflow source 62 is also constituted by a diaphragm utilizing a piezoelectric element (piezo element). While the piezoelectric element constituting this auxiliary airflow source 62 may be of the same size as the piezo element constituting each airflow source 61 for allowing air to flow into the corresponding aroma source cartridge 5 loaded in the corresponding cartridge accommodation chamber 47, a piezo element larger than that of each airflow source 61 can also be used.

As shown in FIG. 4, an auxiliary airflow path 412, serving as a passage through which air discharged from the nozzle of the auxiliary airflow source 62 (odorless air) passes, is formed in the central member 411. The auxiliary airflow path 412 is a path that linearly connects the nozzle of the auxiliary airflow source 62 with the emission port 441. When the auxiliary airflow source 62 is driven, odorless air is discharged from the nozzle of the auxiliary airflow source 62 into the auxiliary airflow path 412. This odorless air flows directly to the emission port 441 and is therefore emitted from the emission port 441, causing substantially no reduction of pressure. As described above, using the larger piezo element constituting the auxiliary airflow source 62 makes it possible to increase the amount of discharged odorless air and to enhance the functions such as the acceleration of aromas, the density adjustment of aroma components, and aroma elimination.

Figure 5:
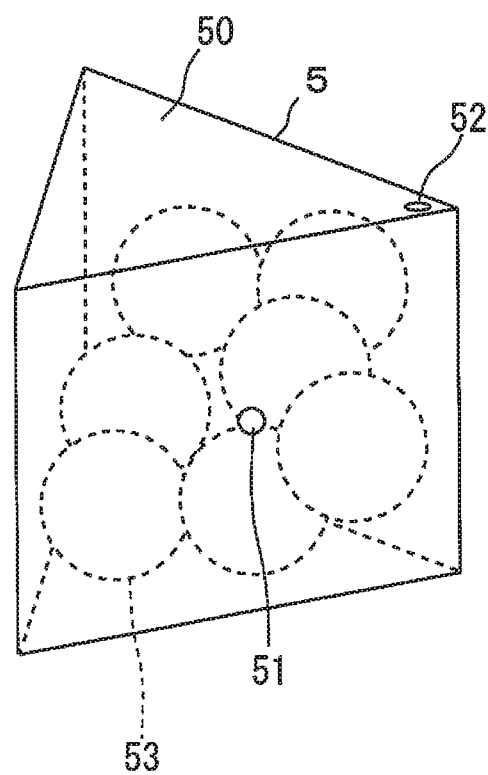
FIG. 5 is a perspective view of an aroma source cartridge.

As shown in FIG. 5, each aroma source cartridge 5 includes a container main body 50 formed of synthetic resin such as polyethylene or polypropylene. In the present embodiment, the container main body 50 is formed in a triangular prism shape to be loadable in the cartridge accommodation chamber 47. The container main body 50 is provided with an air inlet 51. This air inlet 51 is disposed at a position corresponding to the nozzle of the airflow source 61 when the aroma source cartridge 5 is loaded in the cartridge accommodation chamber 47.

As shown in FIG. 5, an aroma emission port 52 is provided at a corner of an upper end of the container main body 50. This aroma emission port 52 is disposed at a position corresponding to the aroma path 471 when the aroma source cartridge 5 is loaded in the cartridge accommodation chamber 47.

Solid-like aroma sources 53 are filled in the interior of the container main body 50. The solid-like aroma source 53 is manufactured by, for example, infiltrating a liquid aroma material into a granular porous body and holding the liquid aroma material in an outer surface and fine pores of the porous body. As the aroma material, a natural aroma material, a synthetic aroma material, and a mixed aroma material thereof can be used. As the porous body, a granular material such as calcium silicate can be utilized. The grain size and shape of the porous body are not limited in particular. With the use of the solid-like aroma source 53, an aroma material (an aroma component) can be gradually emitted from the aroma source 53 over a long duration.

When the aroma source cartridge 5 is loaded in the cartridge accommodation chamber 47 of the display main body 40, the sliding cover 42 is opened to accommodate the aroma source cartridge 5 into the cartridge accommodation chamber 47. Thereafter, the sliding cover 42 is closed, so that the loading of the aroma source cartridge 5 is completed.

After the aroma source cartridge 5 is loaded in the cartridge accommodation chamber 47, if an alternating voltage is applied to the piezoelectric element of the airflow source 61, then the diaphragm is bent and vibrated at a high speed. This operation allows high-pressure air to be delivered at a high speed into the aroma source cartridge 5 through the air inlet 51 from the nozzle of the airflow source 61. The air in the aroma source cartridge 5 contains a gaseous aroma component volatilized from the aroma source 53, and the air containing such an aroma component (aroma) is discharged from the aroma emission port 52 into the aroma path 471.

At the same time or at a shifted time, the auxiliary airflow source 62 is driven. The odorless air discharged from the nozzle of the auxiliary airflow source 62 flows directly to the emission port 441 through the linear auxiliary airflow path 412. The aroma discharged from the aroma emission port 52 into the aroma path 471 is merged with the odorless air discharged from the auxiliary airflow source 62, accelerated, and then emitted vigorously and rectilinearly from the emission port 441. Then, when the application of the voltage to the piezoelectric element of the airflow source 61 is stopped, the emission of the aroma from the emission port 441 is also stopped instantaneously. Alternatively, the odorless air is kept being discharged from the auxiliary airflow source 62 while the aroma emitted from the aroma source cartridge 5 is stopped by stopping the airflow source 61, whereby the aroma emitted from the emission port 441 can be dispersed to eliminate the odor. This makes it possible to control the aroma limited in terms of space and time.

In the present embodiment, the six cartridge accommodation chambers 47, 47 . . . are provided which can accommodate the six aroma source cartridges 5, 5 . . . . Thus, six types of aromas can be presented individually as a matter of course, and also, aromas from the respective cartridge accommodation chambers 47 can be mixed and then presented by operating the airflow sources 61, 61 . . . of the plurality of cartridge accommodation chambers 47, 47 . . . at the same time or at shifted times. Moreover, the proportion in which aromas are mixed can be changed such as by adjusting a voltage to be applied to the airflow sources 61, 61 . . . and a duty ratio thereof. Further, the density of aromas emitted from the aroma source cartridges 5 can be adjusted by adjusting the amount of odorless air blown from the auxiliary airflow source 62.

{3. Standardization of Aroma Number}

Aroma numbers (ACIN: Aroma Cartridge Identifier Numbers) denote codes of aromas standardized in the content sharing system 100. That is, the aroma numbers are assigned to the aroma source cartridges 5 loaded in the olfactory display 4 in accordance with types of the aromas filled in those aroma source cartridges 5. If a user specifies an aroma number, the user can purchase an aroma source cartridge 5 that he/she purchased in the past or an aroma source cartridge 5 that another person recommended him/her to purchase. All types of aromas used in the content sharing system 100 are coded. That is, all the types of aroma source cartridges 5 used in the content sharing system 100 are assigned with aroma numbers (ACIN). Thus, when reproducing the aroma-added content 200 even in the terminal device 3B, which is in a remote location from the terminal device 3A, it is possible to reproduce the same aroma by utilizing the aroma number (ACIN). It is noted that the aroma sources 53 filled in the container main body 50 of the aroma source cartridge 5 are exchangeable, and the aroma source cartridge 5 can be reused.

FIG. 6 is a diagram showing standardized aroma numbers (ACIN). The aromas used in the content sharing system 100 are coded in three-level classifications: large, middle, and small classifications. The large classification is classified into two categories: "natural" or "synthetic." Each of the natural and synthetic categories is classified into categories of the middle classification: "citrus", "drink", "flower", "food", "fruit", "green" . . . etc. The citrus is classified into categories of the small classification: "bergamot", "citronella", "grapefruit", "kabosu (*Citrus sphaerocarpa*), "lemon", "lime" . . . etc. The bergamot is assigned with N-CT1 as the aroma number, and the citronella is assigned with N-CT2 as the aroma number. As a matter of course, the codes of the aroma numbers (ACIN), the code system, the classifications and the like shown in FIG. 6 are one example.

The aroma numbers (ACIN) shown in FIG. 6 are stored in the server 10 and the terminal device 3 as an aroma number table 210. Even a user present in a remote location can share the identical or approximate aroma by sharing the aroma number table 210.

{4. Registration of Aroma Number}

A user utilizing the content sharing system 100 purchases the aroma source cartridges 5, 5 . . . loaded in the olfactory display 4. The aroma source cartridges 5 are filled with various aroma components. The aroma components accommodated in the aroma source cartridges 5 are assigned with the standardized aroma numbers using FIG. 6.

The user loads the purchased aroma source cartridges 5, 5 . . . into the display main body 40 of the olfactory display 4. As described above, the six aroma source cartridges 5, 5 . . . can be loaded in the display main body 40 of the present embodiment.

Figure 7:
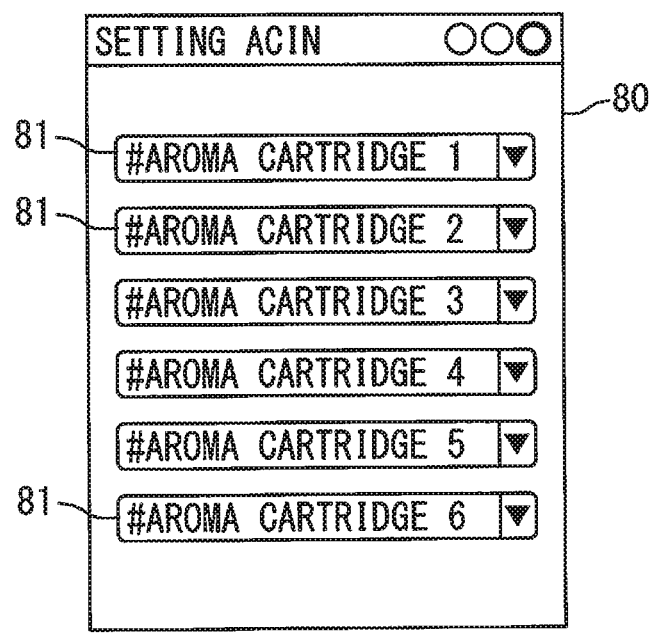
FIG. 7 is a diagram showing a setting screen of aroma source cartridges displayed on a display of a terminal device.

Then, the user starts a setting program SP for setting the olfactory display 4 (shown in FIG. 10) on the terminal device 3 connected with the olfactory display 4. FIG. 7 is a diagram showing a setting screen 80 of the setting program SP displayed on a monitor of the terminal device 3. As shown in FIG. 7, the user performs, on the setting screen 80, an operation of specifying the aroma numbers of the aroma source cartridges 5, 5 . . . loaded in the cartridge accommodation chambers 47, 47 . . . .

As described above, the cartridge accommodation chamber numbers are printed on the cartridge accommodation chambers 47, 47 . . . of the display main body 40 such that the user can recognize the cartridge accommodation chambers 47, 47 . . . . The user recognizes each cartridge accommodation chamber number and sets on the setting screen 80 the aroma number of an aroma source cartridge 5 loaded in the corresponding cartridge accommodation chamber 47.

Figure 8:
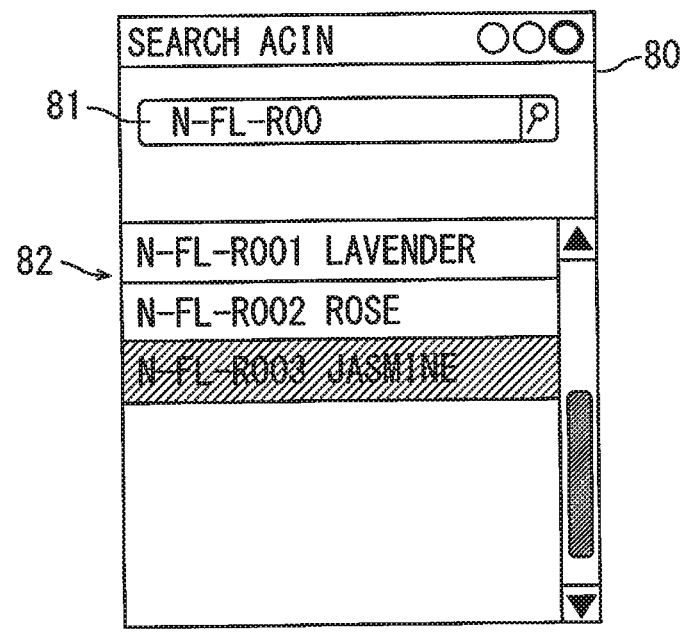
FIG. 8 is a diagram showing the setting screen of aroma source cartridges displayed on the display of the terminal device.

For example, when the user sets the aroma source cartridge 5 loaded in the cartridge accommodation chamber 47 of cartridge accommodation chamber number {1}, the user selects a pulldown menu of an item displayed as "Aroma Cartridge 1" on the setting screen 80 of FIG. 7. Accordingly, an aroma number list 82 is displayed as shown in FIG. 8. The user selects the aroma number of the loaded aroma source cartridge 5 from the aroma number list 82. Thus, the aroma number of the aroma source cartridge 5 loaded in the cartridge accommodation chamber 47 of cartridge accommodation chamber number {1} is registered. By performing the similar operation, the aroma numbers of the aroma source cartridges 5 loaded in the cartridge accommodation chambers 47 of cartridge accommodation chamber numbers {2} to {6} are registered. The aroma numbers of the aroma source cartridges 5 loaded in the cartridge accommodation chambers 47 of cartridge accommodation chamber numbers {1} to {6} are stored as setting information SI (shown in FIG. 10) in the terminal device 3.

{5. Configuration and Processing Flow of Content Sharing System}

A processing flow of the content sharing system 100 of the present embodiment will be described below. As has been explained using FIG. 1, the terminal device 3A and the terminal device 3B are connected to the content sharing system 100. Explanation is herein made on a case, taken as an example, where the terminal device 3A edits and generates an aroma-added content 200 in which aroma reproduction information is added in addition to video information and sound information, and uploads the aroma-added content 200 to the server 10. Also, explanation is made on a case, taken as an example, where the terminal device 3B downloads the aroma-added content 200 uploaded by the terminal device 3A from the server 10 and reproduces the downloaded aroma-added content 200.

Figure 9:
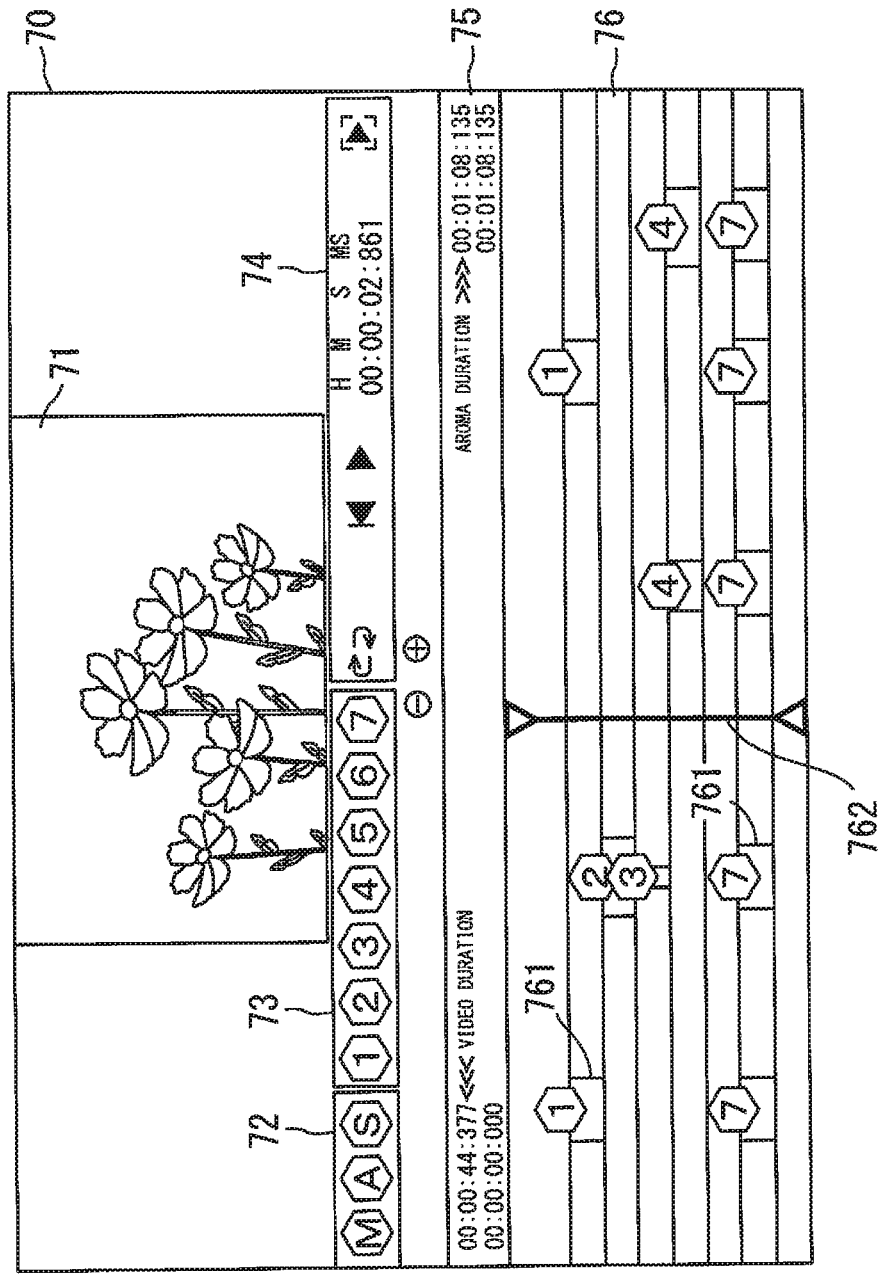
FIG. 9 is a diagram showing a user interface of a content player displayed on the display of the terminal device.

FIG. 9 is a diagram showing a user interface 70 of a content player CP displayed on the displays of the terminal devices 3A and 3B. The content player CP is a program for reproducing an aroma-added content 200 and is installed in the terminal devices 3A and 3B. A function unit in which the content player CP is implemented by utilizing hardware resources of a CPU 31, a memory 32 and the like of the terminal device 3 corresponds to a "content reproducer" of the present invention.

Figure 10:
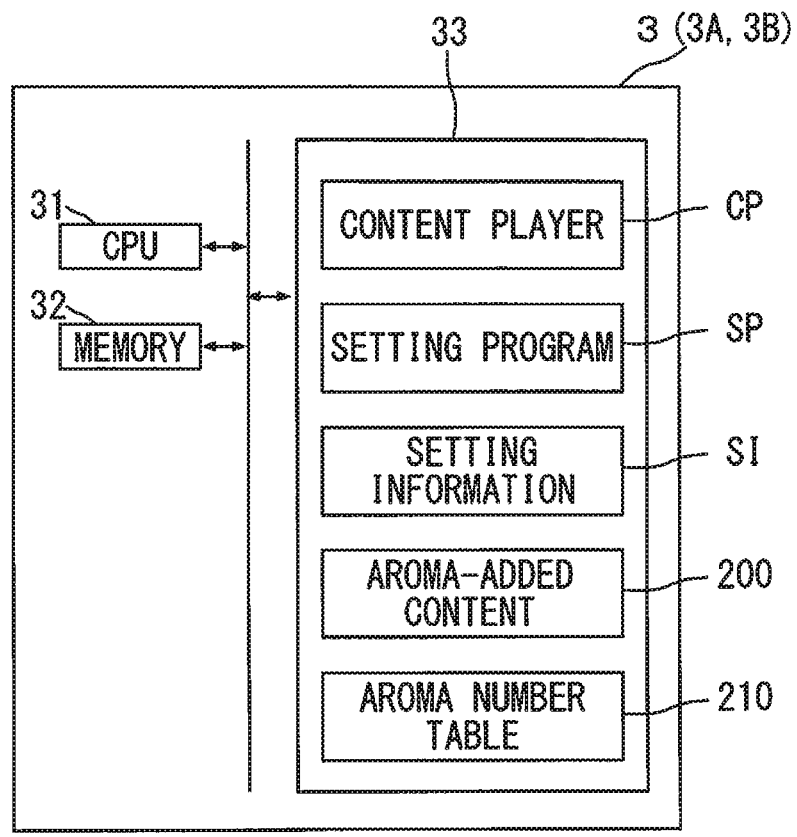
FIG. 10 is a block diagram showing an internal structure of the terminal device.

FIG. 10 is a functional block diagram of the terminal device 3 (3A or 3B). The terminal device 3 includes the CPU 31, the memory 32, and an auxiliary storage device 33 such as a hard disk drive (HDD) or a solid state drive (SDD). The content player CP and the setting program SP are installed in the auxiliary storage device 33. The setting information SI and the aroma number table 210 are stored in the auxiliary storage device 33. The aroma-added content 200, which has been downloaded from the server or self-edited and generated, are stored in the auxiliary storage device 33. The terminal device 3 can reproduce the aroma-added content 200 by executing the content player CP utilizing the hardware resources of the CPU 31 and the memory 32.

An edition that enables only reproduction of the aroma-added content 200 and an edition that enables reproduction as well as edition and generation of the aroma-added content 200 are prepared for the content player CP. In the present embodiment, the edition that enables the reproduction as well as the edition and generation of the aroma-added content is installed in the terminal devices 3A and 3B. A user who does not intend to edit or generate the aroma-added content 200 but intends to only reproduce the aroma-added content 200 may install in the terminal device 3 the edition that enables only the reproduction of the aroma-added content 200.

As shown in FIG. 9, the user interface 70 of the content player CP includes a video reproduction area 71, a data operation menu 72, an aroma selection menu 73, a video control area 74, a reproduction duration display area 75, and a timeline display area 76. The data operation menu 72 and the aroma selection menu 73 are menus utilized when the aroma-added content 200 is edited and generated.

The video reproduction area 71 is an area in which a video included in the aroma-added content 200 is reproduced. A sound included in the aroma-added content 200 is output from a speaker, not shown, included in the terminal device 3. "Aroma codes" that indicate at what time point and how long an aroma specified by an aroma number (ACIN) is to be emitted, as information relating to the aroma, are added to the aroma-added content 200. When the aroma-added content 200 is reproduced, aromas are emitted from the olfactory display 4 based on the aroma codes. The aroma codes correspond to "aroma reproduction information" in the present invention. Many aroma codes corresponding to various scenes constitute aroma data.

The data operation menu 72 displays a video information and/or sound information reference icon (M), an aroma data reference icon (A), and an aroma data storage icon (S). A user can read video/sound information by selecting the video/sound information reference icon (M). As for the video/sound information, for example, data stored in the auxiliary storage device 33 of the terminal device 3 may be read, or data downloaded from any of sites connected to the Internet 2 may be read.

The user can read aroma data 201 by selecting the aroma data reference icon (A). The aroma data 201 is data in which the aroma codes being "aroma reproduction information" are recorded. More specifically, the aroma data 201 is data constituted by a plurality of aroma codes. The user can store edited aroma data 201 by selecting the aroma data storage icon (S). The edited aroma data 201 is stored, as the aroma content 200 with video information and sound information added, into the auxiliary storage device 33 of the terminal device 3.

Figure 11:
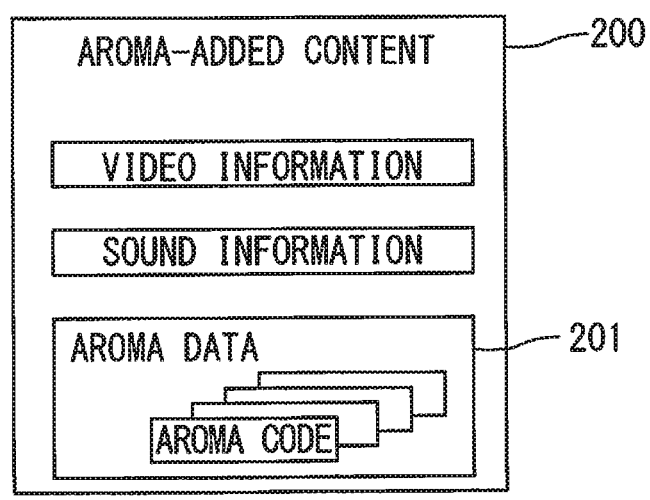
FIG. 11 is a diagram showing a data structure of an aroma-added content.

FIG. 11 is a diagram showing a data structure of the aroma-added content 200. As shown in FIG. 11, the aroma-added content 200 is configured to include the video information, the sound information, and the aroma data 201 constituted by the aroma codes (aroma reproduction information).

FIG. 9 is referred to again. The aroma selection menu 73 displays icons for selecting the aromas of cartridge accommodation chamber numbers {1} to {6}. The aromas of the cartridge accommodation chamber numbers {1} to {6} correspond to the aroma source cartridges 5, 5 . . . respectively loaded in the cartridge accommodation chambers numbered {1} to {6}. A cartridge accommodation chamber number {7} corresponds to a booster (odorless), i.e., air discharged from the aforementioned auxiliary airflow source 62.

The video control area 74 displays icons indicating repeated reproduction, fast-rewinding, and reproduction. The video control area 74 is also provided with an area displaying a video reproduction duration.

The reproduction duration display area 75 is provided with an area that displays a reproduction duration of video (Video Duration) and an area that displays a reproduction duration of aroma data 201 (Aroma Duration).

The timeline display area 76 displays a recorded content of aroma data 201 on a time axis. The user drags and drops the icons of the cartridge accommodation chamber numbers {1} to {6} displayed on the aroma selection menu 73 to the timeline display area 76, so that the user can place the aromas on the time axis and edit the aroma data 201. In FIG. 9, the time axis proceeds from left to right. In the aroma data 201 shown in FIG. 9, information is recorded as to a procedure in which, first, an aroma corresponding to the cartridge accommodation chamber number {1} and odorless air (air as the booster) corresponding to the cartridge accommodation chamber number {7} are emitted simultaneously, and then, aromas corresponding to the cartridge accommodation chamber numbers {2} and {3} and the odorless air corresponding to the cartridge accommodation chamber number {7} are emitted simultaneously, and after a short period of time, an aroma corresponding to the cartridge accommodation chamber number {4} and the odorless air corresponding to the cartridge accommodation chamber number {7} are emitted simultaneously. Subsequently, in the aroma data 201 shown in FIG. 9, information is recorded as to a subsequent procedure in which the aroma corresponding to the cartridge accommodation chamber number {1} and the odorless air are emitted simultaneously again, and finally the aroma corresponding to the cartridge accommodation chamber number {4} and the odorless air are emitted simultaneously.

An emission duration bar 761 is displayed on each of aroma icons displayed in the timeline display area 76. The emission duration bar 761 represents the emission duration of the aromas by the lengths of the bar. The user selects an aroma icon displayed in the timeline display area 76, so that a property of the selected aroma is displayed and the user can perform settings with respect to emission of the aroma. Setting items relating to the emission of the aroma are an emission time, an emission duration, an emission density, and the like. Aroma codes are generated, respectively, for the aroma icons arranged in the timeline display area 76. A collection of the aroma codes corresponding to the number of the aroma icons constitutes the aroma data 201.

The emission density represents at what percentage the emission is performed with a full emission density defined as 100%. By moving a cursor of an operation device such as a mouse to the emission duration bar 761 and clicking a right button, the setting screen of the emission density may be displayed, or alternatively, the emission density may be displayed in percentage for each video reproduction area 71 in a blank space on the right side of the video reproduction area 71.

Furthermore, a time progress bar 762 representing a reproduction time at which a content is reproduced is displayed in the timeline display area 76. A display position of the time progress bar 762 represents the reproduction time. When the time progress bar 762 comes into contact with an aroma icon arranged in the timeline display area 76, an aroma and/or odorless air specified by the aroma icon is emitted. This time progress bar 762 is considered to be of either a type in which the bar itself moves rightward as time passes or a type in which the background timeline display area 76 moves leftward as time passes while the bar itself is fixed. Alternatively, the time progress bar 762 can be configured such that a colored marker moves rightward directly below the timeline display area 76 as time passes.

FIG. 12 is a diagram showing an "Aroma Code" recorded in the aroma data 201. An aroma number (ACIN), an emission time (Diffuse), an emission duration (Duration), and an emission density (Density) are recorded in the aroma code.

The emission time (Diffuse) represents a time at which an aroma specified by the aroma number is emitted. The emission time (Diffuse) is a relative time relative to a reproduction start time of the aroma-added content 200. In the example of FIG. 12, it is recorded that the emission of an aroma of aroma number N-XXX1 is started when five minutes have passed since the start of reproduction of the aroma-added content 200. The emission duration (Duration) represents a period in which the aroma specified by the aroma number is emitted. In the example of FIG. 12, it is recorded that the aroma of the aroma number N-XXX1 is emitted for three seconds. More specifically, in the example of FIG. 12, the emission of the aroma of the aroma number N-XXX1 is started when five minutes have passed since the start of the reproduction of the aroma-added content 200, and thereafter, the emission of the aroma is continued for three seconds. The emission density (Density) represents the density of the aroma of the aroma number N-XXX1 when the aroma is emitted. The density is specified between 0 to 100%. The aroma density is adjusted by control of the amount of air discharged from the auxiliary airflow source 62, as described above.

The user edits and generates the aroma-added content 200 by performing the aforementioned operation by utilizing the content player CP. The aroma codes are added to the aroma-added content 200 in addition to the video information and the sound information. If the aroma-added content 200 is reproduced in the content player CP, a video is reproduced in the video reproduction area 71. In synchronization with the reproduction of the video, a sound is reproduced from the speaker of the terminal device 3. In synchronization with the reproduction of the video and the sound, an aroma is emitted based on the aroma code. More specifically, the content player CP controls the olfactory display 4 based on the aroma code so that the aroma synchronized with the reproduction of the video and the sound is emitted.

Figure 13:
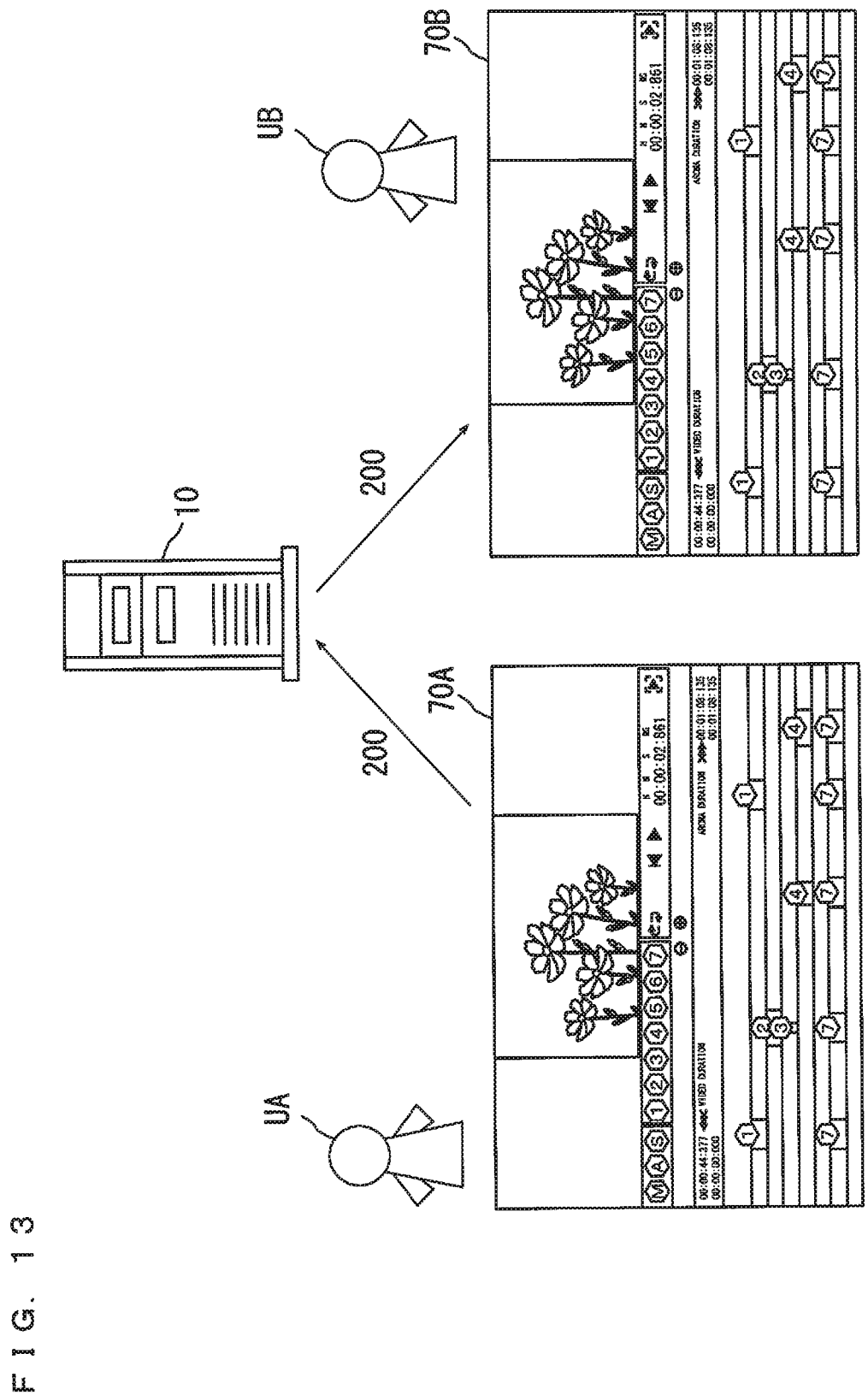
FIG. 13 is a diagram showing an image of utilization of the content sharing system.

FIG. 13 is a diagram showing a manner in which an aroma-added content 200 is shared between a user UA who utilizes the terminal device 3A and a user UB who utilizes the terminal device 3B. In FIG. 13, the user UA edits and generates the aroma-added content 200 with reference to the user interface 70A by utilizing the content player CP installed in the terminal device 3A. The user UA operates the terminal device 3A to upload the edited and generated aroma-added content 200 to the server 10. The server 10 stores the uploaded aroma-added content 200 into a storage 11. The aroma-added content 200 includes the aroma codes shown in FIG. 11. In the present embodiment, the content player CP enables the edition and generation and the upload operation of the aroma-added content 200. A function in which the content player CP edits and generates the aroma-added content 200 by utilizing the hardware resources of the CPU 31 and the memory 32 corresponds to the "content generator" of the present invention.

The user UB operates the terminal device 3B to download the aroma-added content 200 uploaded by the terminal device 3A from the server 10. The user UB starts the content player CP in the terminal device 3B to reproduce the downloaded aroma-added content 200.

The display of the terminal device 3B displays the user interface 70 shown in FIG. 9. Then, a video included in the aroma-added content 200 is reproduced in the video reproduction area 71. Also, a sound included in the aroma-added content 200 is reproduced from the speaker of the terminal device 3B.

In the terminal device 3B, the content player CP controls the olfactory display 4 so that the olfactory display 4 emits an aroma in synchronization with the reproduction of the video and the sound. More specifically, the content player CP controls the olfactory display 4 so that the olfactory display 4 emits an aroma based on the aroma code included in the aroma-added content 200.

The content player CP checks whether the aroma source cartridge 5 of an aroma number identical to the aroma number (ACIN) recorded in the aroma code is loaded in the olfactory display 4 connected to the terminal device 3. More specifically, the content player CP checks the aroma number of each of the aroma source cartridges 5, 5 . . . accommodated in the respective cartridge accommodation chambers 47, 47 . . . with reference to the setting information SI.

In the case where the aroma source cartridge 5 of the aroma number identical to the aroma number recorded in the aroma code is loaded, the content player CP controls the olfactory display 4 so that an aroma is emitted from the aroma source cartridge 5 of the identical aroma number. That is, the aroma of the aroma number recorded in the aroma code is reproduced in accordance with the emission time, the emission duration, and the density recorded in the aroma code in synchronization with the video and the sound.

In the case where the aroma source cartridge 5 of the aroma number identical to the aroma number recorded in the aroma code is not loaded, the content player CP controls the olfactory display 4 so that an approximate (or close) aroma is emitted from the aroma source cartridge 5 filled with the approximate (or close) aroma.

Figure 14:
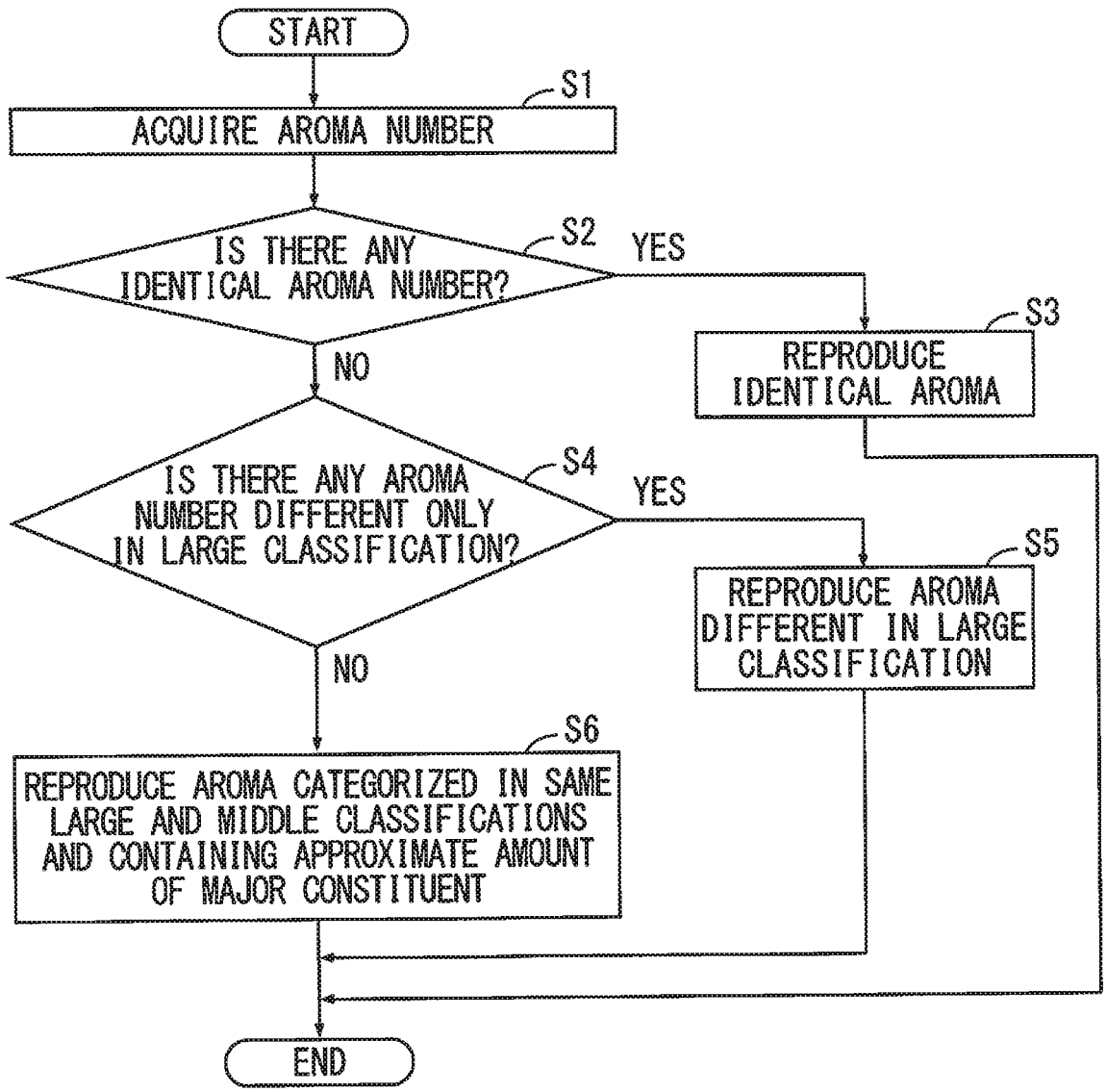
FIG. 14 is a flowchart showing a selection algorithm of an aroma source cartridge.

FIG. 14 is a flowchart showing a selection algorithm of the aroma source cartridge 5 executed by the content player CP. The content player CP first acquires an aroma number to be reproduced from the aroma codes included in the aroma-added content 200 (step S1). The content player CP checks whether an aroma source cartridge 5 of a number identical to the acquired aroma number is loaded in the olfactory display 4 (step S2). The content player CP recognizes the aroma number of the aroma source cartridge 5 loaded in the connected olfactory display 4 with reference to the setting information SI.

In the case where the aroma source cartridge 5 of the number identical to the acquired aroma number is loaded, the content player CP controls the olfactory display 4 so that the aroma source cartridge 5 of the identical number emits an aroma (step S3), and thus aroma emission processing is terminated.

In the case where the aroma source cartridge 5 of the number identical to the acquired aroma number is not loaded, the content player CP checks whether an aroma source cartridge 5 of an aroma number, which is different only in large classification, is loaded (step S4). For example, assuming that the aroma number recorded in the aroma code is bergamot: N-CT1 as shown in FIG. 6, that is, assuming that the aroma number corresponding to "natural"-"citrus"-"bergamot" is recorded, when an aroma source cartridge 5 of the identical aroma number is not loaded, the content player CP checks whether an aroma source cartridge 5 filled with bergamot: S-CT1 of "synthetic" in the large classification is loaded. That is, the content player CP checks whether the aroma source cartridge 5 corresponding to "synthetic"-"citrus"-"bergamot" is loaded.

In the case where the content player CP can recognize that the aroma source cartridge 5 of the aroma number, which is different only in the large classification, is loaded, the content player CP controls the olfactory display 4 so that the aroma source cartridge 5 of the aroma number, which is different only in the large classification, emits the aroma (step S5), and thus the aroma emission processing is terminated.

In the case where the aroma source cartridge 5 of the aroma number, which is different only in the large classification, is not loaded, the processing proceeds to step S6. In the step S6, the content player CP selects an aroma source cartridge containing an aroma component which is categorized in the same large and middle classifications and in which blending ratio of its major constituent is close to that of the major constituent of the intended aroma component (step S6), and thus the aroma emission processing is terminated.

For example, assuming that the aroma number recorded in the aroma code is the bergamot: N-CT1 shown in FIG. 6, that is, assuming that the aroma number corresponding to "natural"-"citrus"-"bergamot" is recorded, aroma numbers that are categorized in the same large and middle classifications as those of this aroma number correspond to "citronella", "grapefruit", "kabosu", "lemon", "lime" . . . and the like, which are classified in "natural"-"citrus." The content player CP selects, among those listed aroma numbers, an aroma source cartridge 5 of an aroma number of an aroma, of which blending ratio of its major constituent is the most approximate or closest to that of the major constitute of the aroma number corresponding to "natural"-"citrus"-"bergamot".

In order to execute the step S6, the blending ratio of the major constituent of the aroma of each aroma number is recorded as associated data in the aroma number table 210. The content player CP acquires information as to the major constituent of the aroma of each aroma number with reference to the associated data in the aroma number table 210, and executes the processing of the step 6.

The content player CP executes the foregoing algorithm, whereby the olfactory display 4 connected to the terminal device 3B can emit the aroma, which is identical or approximate to the aroma that the user UA has intended to edit and generate in the terminal device 3A. Thus, even if the terminal device 3B is placed in a remote location, it is possible to reproduce the aroma-added content 200 including the synchronized video, sound, and aroma, which has been edited and generated in the terminal device 3A by the user UA.

{6. Recommendation Service of Aroma-Added Content}

As has been described above, the user UA and the user UB in the remote locations can share the aroma-added content 200, which reproduces the identical or approximate aroma by utilizing the content sharing system 100 of the present embodiment. It is also possible to provide a recommendation service of the aroma-added content 200 by expanded utilization of this system.

The recommendation service of the aroma-added content 200 is a service for recommending an aroma-added content 200 that can be reproduced by the olfactory display 4 owned by a user. Information as to the aroma source cartridges 5 loaded in the olfactory display 4 is stored as the setting information SI in the auxiliary storage device 33 of the terminal device 3. The terminal device 3 transmits the setting information SI to the server 10, so that the information as to the aroma source cartridges 5 loaded in the olfactory display 4 connected to the terminal device 3 can be grasped at the server 10.

Returning to FIG. 1, a presentation program DP of the server 10 installed in the server 10 presents a recommendation list of aroma-added contents 200 reproducible in the olfactory display 4 to the terminal device 3. The presentation program DP presents the recommendation list by utilizing, for example, a WEB application. An aroma-added content 200 with the highest recommendation value refers to the case where the aroma source cartridges 5, corresponding to all of the aroma numbers recorded in the aroma data 201 included in the aroma-added content 200, are loaded in the olfactory display 4. For example, it is the case where six types of aroma numbers are recorded in the aroma data 201 of the aroma-added content 200, and all of the aroma source cartridges 5 corresponding to those six types of aroma numbers are loaded in the olfactory display 4.

An aroma-added content 200 with the second highest recommendation value refers to the case where the aroma source cartridges 5 corresponding to the aroma numbers recorded in the aroma data 201 included in the aroma-added content 200, except for one aroma number, are loaded in the olfactory display 4. For example, it is the case where six types of aroma numbers are recorded in the aroma data 201 of the aroma-added content 200, and the aroma source cartridges 5 corresponding to five of the six types of aroma numbers are loaded in the olfactory display 4. In this way, it is possible to recommend the aroma-added content 200 for the user by suitably varying a recommendation level depending on the number of the loaded corresponding aroma source cartridges 5 and/or the selection algorithm of the aroma source cartridges 5.

{7. Platform of Aroma-Added Content}

As has been described in the aforementioned embodiment, the users in the remote locations can share the aroma-added content 200, in which the aroma is added to the video and/or the sound, by utilizing the content sharing system 100. In the aforementioned embodiment, the user UA and the user UB have reproduced the aroma-added contents 200 by utilizing the content players CP installed in the terminal devices 3A and 3B, respectively.

The server 10 provides an API and a software development kit (SDK) for reproducing an aroma-added content 200. The user can program a software such that the aroma-added content 200 can be reproduced in various applications by downloading the API/SDK 220 stored in the storage 11 of the server 10.

For example, the user can publish a content in which the aroma-added content 200 is buried to be reproducible in a social networking service (SNS). Alternatively, the user can publish the content in which the aroma-added content 200 is buried to be reproducible on his/her personal website or blog. As described above, since all the aroma source cartridges 5 are standardized by the aroma numbers shown in FIG. 6, a third person who has downloaded these published aroma-added contents 200 can enjoy an aroma-added content 200 that is similar to the aroma-added content intended by an editor/generator.

{8. Others}

The aroma-added content 200 may be in a mode in which video information, sound information, and aroma codes are packaged. Alternatively, the aroma-added content 200 may be in a mode in which aroma codes are incidentally added to data in which video information and sound information are packaged.

In the aforementioned embodiment, the explanation has been made of the configuration, in which the terminal device 3A uploads the aroma-added content 200 to the server 10 while the terminal device 3B downloads the aroma-added content 200. As for downloading, there are some modes in which various application software or WEB browsers are utilized, and thus the modes are not limited in particular. For example, such a configuration may be applied that the aroma-added content 200 is shared between the terminal device 3A and the terminal device 3B via e-mail. In this case, the server 10 functions as a mail server.

In the aforementioned embodiment, the example of the system for sharing the aroma-added content 200 in which the aroma reproduction information is added to the video information and/or the sound information has been explained. However, the present invention is applicable to a system for sharing an aroma ("aroma sharing system") by sharing only aroma reproduction information not being added to video information or sound information. That is, since the aromas are coded by the aroma numbers, even the users in remote locations can share the same aroma by sharing the aroma reproduction information including the aroma numbers.

In the aforementioned embodiment, the aroma-added content 200, in which the aroma reproduction information is added to the video information and/or the sound information, has been reproduced by the "content reproducer." In the case where only the aroma reproduction information is shared without being added to the video information or the sound information, the "reproducer" of the present invention controls the olfactory display 4 so that the olfactory display 4 emits an aroma based on the aroma reproduction information. The details of the processing of emitting the aroma based on the aroma reproduction information are similar to those of the aforementioned embodiment. While the aroma is emitted based on the aroma reproduction information in synchronization with the video information and/or the sound information in the aforementioned embodiment, the "reproducer" of the "aroma sharing system" emits the aroma based on the aroma reproduction information without being in synchronization with the video information and/or the sound information. While the content player CP can edit and generate the aroma reproduction information synchronized with the video information and/or the sound information in the aforementioned embodiment, the content player CP edits and generates the aroma reproduction information without being in synchronization with the video information and/or the sound information in the "aroma sharing system."

In the aforementioned embodiment, the example of the case where the aroma-added content 200 is stored in the server 10 connected to the Internet 2 has been explained. However, the configuration that includes the server 10 is not essential for the configuration of the "aroma-added content sharing system" of the present invention. In the "aroma-added content sharing system" of the present invention, the "olfactory unit" that includes the terminal device 3 and the olfactory display 4 only has to be connected via a network. The "olfactory unit" can reproduce the aroma based on the aroma reproduction information by sharing the aroma-added content via the network. Thus, the same aroma can be reproduced in synchronization with the video information and/or sound information among different users.

Similarly, the configuration that includes the server 10 is not essential for the configuration of the "aroma sharing system" of the present invention. In the aroma sharing system of the present invention, the "olfactory unit" that includes the terminal device 3 and the olfactory display 4 only has to be connected via the network. The "olfactory unit" can reproduce the same aroma among different users by sharing the aroma reproduction information via the network.

While preferred embodiments of the present invention have been described above, it is to be understood that variations and modifications will be apparent to those skilled in the art without departing the scope and spirit of the present invention. The scope of the present invention, therefore, is to be determined solely by the following claims.

I claim:

1. A system that shares an aroma, comprising:
a plurality of olfactory units;
a network that connects the plurality of olfactory units,
wherein each olfactory unit includes
an olfactory display in which a plurality of aroma source cartridges can be loaded, and
a terminal device that controls the olfactory display,
wherein the terminal device includes
a reproducer that reproduces an aroma based on aroma reproduction information including an aroma number standardized in the system in order to specify a type of the aroma to be reproduced,
wherein the reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information,
when the aroma source cartridge for reproducing an aroma corresponding to the aroma number recorded in the aroma reproduction information is not loaded in the olfactory display, the reproducer determines to use an aroma source cartridge for reproducing an aroma approximate to the corresponding aroma to reproduce the approximate aroma by utilizing a preset algorithm, and each olfactory unit transmits the aroma reproduction information to a different olfactory unit via the network to share the aroma reproduction information with the different olfactory unit.

2. The aroma sharing system according to claim 1, wherein at least one of the terminal devices includes a generator that edits the aroma reproduction information including the aroma number standardized in the system and generates the edited aroma reproduction information.

3. The aroma sharing system according to claim 2, wherein the aroma reproduction information generated by the generator of the terminal device is transmitted to another terminal device.

4. The aroma sharing system according to claim 1, wherein the olfactory display includes a plurality of cartridge accommodation chambers for loading the plurality of aroma source cartridges in the chambers, and
the terminal device includes a setter that sets a type of an aroma filled in each aroma source cartridge loaded in each cartridge accommodation chamber by using the aroma number.

5. A system that shares an aroma, comprising:
a plurality of olfactory units;
a network that connects the plurality of olfactory units; and
a server connected to the network,
wherein each olfactory unit includes
an olfactory display in which a plurality of aroma source cartridges can be loaded, and
a terminal device that controls the olfactory display,
the server includes a storage that stores aroma reproduction information including an aroma number standardized in the system in order to specify a type of an aroma to be reproduced,
the terminal device includes a reproducer that reproduces an aroma based on the aroma reproduction information downloaded from the server,
wherein the reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information,
when the aroma source cartridge for reproducing an aroma corresponding to the aroma number recorded in the aroma reproduction information is not loaded in the olfactory display, the reproducer determines to use an aroma source cartridge for reproducing an aroma approximate to the corresponding aroma to reproduce the approximate aroma by utilizing a preset algorithm, and
each olfactory unit transmits the aroma reproduction information to a different olfactory unit via the server to share the aroma reproduction information with the different olfactory unit.

6. The aroma sharing system according to claim 5, wherein at least one of the terminal devices includes a generator that edits the aroma reproduction information including the aroma number standardized in the system and generates the edited aroma reproduction information.

7. The aroma sharing system according to claim 6, wherein the aroma reproduction information generated by the generator of the terminal device is transmitted to another terminal device.

8. The aroma sharing system according to claim 5, wherein the olfactory display includes a plurality of cartridge accommodation chambers for loading the plurality of aroma source cartridges in the chambers, and the terminal device includes a setter that sets a type of an aroma filled in each aroma source cartridge loaded in each cartridge accommodation chamber by using the aroma number.

9. A system that shares an aroma-added content for reproducing an aroma synchronized with video information and/or sound information, the system comprising:

a plurality of olfactory units; and a network that connects the plurality of olfactory units, wherein each olfactory unit includes an olfactory display in which a plurality of aroma source cartridges can be loaded, and a terminal device that controls the olfactory display, wherein the terminal device includes a content reproducer that reproduces an aroma-added content including aroma reproduction information synchronized with video information and/or sound information, wherein the aroma reproduction information includes an aroma number standardized in the system in order to specify a type of an aroma to be reproduced, the content reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information in synchronization with the video information and/or the sound information, when the aroma source cartridge for reproducing an aroma corresponding to the aroma number recorded in the aroma reproduction information is not loaded in the olfactory display, the content reproducer determines to use an aroma source cartridge for reproducing an aroma approximate to the corresponding aroma to reproduce the approximate aroma by utilizing a preset algorithm, and each olfactory unit transmits the aroma-added content including the aroma reproduction information to a different olfactory unit via the network to share the aroma-added content with the different olfactory unit.

10. The aroma-added content sharing system according to claim 9, wherein at least one of the terminal devices includes a content generator that edits the aroma reproduction information including the aroma number standardized in the system, and edits the aroma-added content including the aroma reproduction information synchronized with the video information and/or the sound information to generate the edited aroma-added content.

11. The aroma-added content sharing system according to claim 10, wherein the aroma-added content including the aroma reproduction information generated by the content generator of the terminal device is transmitted to another terminal device.

12. A system that shares an aroma-added content for reproducing an aroma synchronized with video information and/or sound information, the system comprising:

a plurality of olfactory units;

a network that connects the plurality of olfactory units; and a server connected to the network, wherein each olfactory unit includes an olfactory display in which a plurality of aroma source cartridges can be loaded, and a terminal device that controls the olfactory display, the server includes a storage that stores an aroma-added content including aroma reproduction information synchronized with video information and/or sound information, the terminal device includes a content reproducer that reproduces the aroma-added content downloaded from the server, the aroma reproduction information includes an aroma number standardized in the system in order to specify a type of an aroma to be reproduced, the content reproducer determines which aroma source cartridge of the plurality of aroma source cartridges loaded in the olfactory display is to be used to reproduce an aroma based on the aroma number, and allows the aroma to be emitted from the olfactory display based on the aroma reproduction information in synchronization with the video information and/or the sound information, when the aroma source cartridge for reproducing an aroma corresponding to the aroma number recorded in the aroma reproduction information is not loaded in the olfactory display, the content reproducer determines to use an aroma source cartridge for reproducing an aroma approximate to the corresponding aroma to reproduce the approximate aroma by utilizing a preset algorithm, and each olfactory unit transmits the aroma-added content including the aroma reproduction information to a different olfactory unit via the server to share the aroma-added content with the different olfactory unit.

13. The aroma-added content sharing system according to claim 12, wherein at least one of the terminal devices includes a content generator that edits the aroma reproduction information including the aroma number standardized in the system, and edits the aroma-added content including the aroma reproduction information synchronized with the video information and/or the sound information to generate the edited aroma-added content.

14. The aroma-added content sharing system according to claim 13, wherein the aroma-added content including the aroma reproduction information generated by the content generator of the terminal device is transmitted to another terminal device.

15. The aroma-added content sharing system according to claim 12, further comprising a platform that provides an application programming interface for incorporating the aroma-added content uploaded to the server so that the incorporated aroma-added content can be reproduced in another information publishing system.

16. The aroma-added content sharing system according to claim 12, wherein the server includes a presenter that acquires the aroma number of the aroma filled in the aroma source cartridge loaded in the olfactory display to present to the terminal device a list of the aroma-added contents recommended to be reproduced in the terminal device.

\* \* \* \* \*